United States Patent [19]
Graff-Andersen et al.

[11] Patent Number: 5,869,029
[45] Date of Patent: Feb. 9, 1999

[54] DISPERSIBLE WATER-SOLUBLE OR WATER-SWELLABLE POLYMERS AND PROCESS FOR MAKING TOOTHPASTES CONTAINING THEM

[75] Inventors: Arne Graff-Andersen, Koege, Denmark; Jashawant J. Modi, New Castle County, Del.

[73] Assignee: Hercules Incorporated, Wilmington, Del.

[21] Appl. No.: 668,181

[22] Filed: Jun. 21, 1996

[51] Int. Cl.⁶ .............................. A61L 15/00; A61K 7/18; A61K 47/00
[52] U.S. Cl. ............................ 424/52; 514/777; 514/782; 514/781; 514/778; 252/175; 252/164; 252/315.3
[58] Field of Search ............................... 424/52; 514/777, 514/782, 781, 778; 252/175, 164, 315.3

[56] References Cited

U.S. PATENT DOCUMENTS

| | | | |
|---|---|---|---|
| 3,840,657 | 10/1974 | Norfleet | 424/49 |
| 3,850,838 | 11/1974 | Guckenberger et al. | 252/363.5 |
| 4,374,823 | 2/1983 | Harvey et al. | 424/52 |
| 4,701,319 | 10/1987 | Woo | 424/52 |
| 5,030,444 | 7/1991 | Hoyles et al. | 424/49 |
| 5,633,028 | 5/1997 | Wong | 426/99 |
| 5,662,924 | 9/1997 | Rhodes | 424/445 |
| 5,674,999 | 10/1997 | Smith et al. | 536/56 |

FOREIGN PATENT DOCUMENTS

| | | |
|---|---|---|
| 212968A | 8/1984 | Germany . |
| 72044335B | 11/1972 | Japan . |
| 73036167B | 11/1973 | Japan . |
| 2172008 | 9/1986 | United Kingdom . |

*Primary Examiner*—John Kight
*Assistant Examiner*—D. Margaret M. Mach
*Attorney, Agent, or Firm*—Martin F. Sloan

[57] ABSTRACT

This invention provides compositions comprising particulate water-soluble or water-swellable polymer at least partially agglomerated by treatment with at least one polyol, wherein the polyol is present at a level greater than about 10 wt. % based on the total weight of the composition. The particulate water-soluble or water-swellable polymer which has been at least partially agglomerated by treatment with polyol hydrates in water-containing solvents substantially faster than untreated water-soluble or water-swellable polymer, without formation of polymer lumps. The invention further provides an improved process for preparing a toothpaste composition comprising at least one dry, water-soluble or water-swellable polymer, the improvement comprising substituting for the dry, water-soluble or water-swellable polymer, particulate water-soluble or water-swellable polymer which has been at least partially agglomerated by treatment with polyol.

53 Claims, No Drawings ical
DISPERSIBLE WATER-SOLUBLE OR WATER-SWELLABLE POLYMERS AND PROCESS FOR MAKING TOOTHPASTES CONTAINING THEM

FIELD OF THE INVENTION

This invention relates to compositions comprising water-soluble or water-swellable polymers agglomerated by treatment with polyols, and to the use of the compositions in making toothpastes.

BACKGROUND OF THE INVENTION

Toothpaste formulations generally contain dentally acceptable abrasive, humectant, water, and water-soluble polymer which serves as a thickener and binder for the ingredients. A variety of other ingredients such as flavors, sweeteners, preservatives and fluoride are also utilized at low levels. Glycerol and sorbitol (usually as an aqueous solution) are the most commonly used humectants for toothpaste, and depending on the characteristics desired in the product, polyethylene glycol or propylene glycol may be incorporated as well. Two types of toothpaste are widely produced: 1) cream or opaque; and 2) transparent or translucent gel.

The most commonly used thickeners or binders for toothpaste are carboxymethyl cellulose (CMC), hydroxyethyl cellulose (HEC), silica and magnesium aluminum silicate. Carrageenan, xanthan and polyacrylates are also used, but much less widely.

In the manufacturing process for toothpastes, incorporation of the dry water-soluble binder polymer into the composition often presents difficulties because of the tendency for lump formation when the dry polymers are added to and dispersed in aqueous systems. This increases the time required to obtain uniform hydration or dispersion of the binder polymer. Consequently, there is a need in the industry for methods of incorporating water-soluble binder polymers which lead to lump-free products, rapid viscosity development and reduced batch preparation time, and which allow convenient handling of the binder.

Japanese Patent Application No. 73036167 B discloses a composition comprising (1) carboxymethyl cellulose, alginic acid, polyacrylic acid, or a salt thereof, treated by (a) coating with glycerol or alcohol, or (b) coating with starch paste, shellac, gelatin and agar, followed by treatment (a), or (c) coating with a mixture of substances in (a) and substances in (b); (2) alkali carbonate, bicarbonate, phosphate, polyphosphate or alkali salt of EDTA, optionally treated by the methods of (a), (b) and (c); and optionally (3) glucose, sugar, fructose, maltose, mannitol and common salt. When water is added to the composition, it is rapidly wetted and dispersed, and solutions of alginic acid, polyacrylic acid or carboxymethyl cellulose can be obtained rapidly.

Japanese Patent Application No. 72044335 B teaches improving the solubility of a water-soluble polymer by coating it with molten polyhydric alcohol, sugar or emulsion aid. The water-soluble polymers include methyl cellulose, CMC, polyvinyl alcohol, alginic acid salts, polyacrylic acid or its salts, and polyacrylamide. The polyhydric alcohols include sorbitol, mannitol, inositol, and sugars include glucose, sucrose and lactose. The coating substance is used in the amount of 0.5 to 10 wt. %, preferably 3 to 5 wt. % relative to the polymer.

U.S. Pat. No. 3,850,838 to Guckenberger et al. discloses methods for preparing alcohol insoluble hydrocolloids ion the form of readily dispersible and soluble agglomerates, the process comprising intimately combining the hydrocolloid with a carbohydrate binder that is soluble in both water and alcohol and an aqueous alcoholic solvent for the carbohydrate, granulating the resulting mixture, and then drying the resulting agglomerated granules.

None of the above patents teach the use of polyol-agglomerated water-soluble or water-swellable polymer in toothpaste compositions.

SUMMARY OF THE INVENTION

This invention relates to compositions comprising particulate water-soluble or water-swellable polymer at least partially agglomerated by treatment with at least one polyol, wherein the polyol is at a level greater than about 10 wt. % based on the total weight of the composition. The composition is dispersible in solvents substantially faster than the corresponding untreated water-soluble or water-swellable polymer, without formation of polymer lumps.

In another aspect the invention also relates to an improved process for preparing a toothpaste composition comprising at least one dry, water-soluble or water-swellable polymer, the improvement comprising substituting for the dry, water-soluble or water-swellable polymer, particulate water-soluble or water-swellable polymer which has been at least partially agglomerated by treatment with polyol. The particulate water-soluble or water-swellable polymer which has been at least partially agglomerated by treatment with polyol hydrates in water or water-containing solvents substantially faster than the corresponding untreated water-soluble or water-swellable polymer, without formation of polymer lumps.

DETAILED DESCRIPTION OF THE INVENTION

The compositions of this invention comprise particulate water-soluble or water-swellable polymer at least partially agglomerated by treatment with at least one polyol, wherein the polyol is at a level greater than about 10 wt. % based on the total weight of the composition. Agglomeration is defined herein as the aggregation of individual particles resulting in an increase in the particle size of the particulate material.

Any natural or synthetic water-soluble or water-swellable polymer may be employed to prepared the compositions of this invention. Preferred water-soluble or water-swellable polymers are polysaccharides. Useful polysaccharides may include, but are not limited to, cellulose ethers, guar, guar derivatives, locust bean gum, psyllium, gum arabic, gum ghatti, gum karaya, gum tragacanth, carrageenan, agar, algin, xanthan, scleroglucan, dextran, pectin, starch, chitin and chitosan.

Preferred polysaccharides are cellulose ethers, carrageenan, guar, guar derivatives and pectin.

Cellulose ethers for use in the invention include hydroxyethyl cellulose (HEC), hydroxypropyl cellulose (HPC), water soluble ethylhydroxyethyl cellulose (EHEC), carboxymethyl cellulose (CMC), carboxymethylhydroxyethyl cellulose (CMHEC), hydroxypropylhydroxyethyl cellulose (HPHEC), methyl cellulose (MC), methylhydroxypropyl cellulose (MHPC), methylhydroxyethyl cellulose (MHEC), carboxymethylmethyl cellulose (CMMC), hydrophobically modified carboxymethyl cellulose (HMCMC), hydrophobically modified hydroxyethyl cellulose (HMHEC), hydrophobically modified hydroxypropyl cellulose (HMHPC), hydrophobically modified ethylhydroxyethyl cellulose (HMEHEC), hydrophobically modified carboxymethylhydroxyethyl cellulose (HMCMHEC), hydrophobically modified hydroxypropylhydroxyethyl cellulose (HMHPHEC), hydrophobically modified methyl cellulose (HMMC), hydrophobically modified methylhydroxypropyl cellulose (HMMHPC), hydrophobically modified methylhydroxyethyl cellulose (HMMHEC), hydrophobically modified carboxymethylmethyl cellulose (HMCMMC), cationic hydroxyethyl cellulose (cationic HEC) and cationic hydrophobically modified hydroxyethyl cellulose (cationic HMHEC). Preferred cellulose ethers are carboxymethyl cellulose and hydroxyethyl cellulose.

Guar derivatives for use in the invention include carboxymethyl guar (CM guar), hydroxyethyl guar (HE guar), hydroxypropyl guar (HP guar), carboxymethylhydroxypropyl guar (CMHP guar), cationic guar, hydrophobically modified guar (HM guar), hydrophobically modified carboxymethyl guar (HMCM guar), hydrophobically modified hydroxyethyl guar (HMHE guar), hydrophobically modified hydroxypropyl guar (HMHP guar), cationic hydrophobically modified hydroxypropyl guar (cationic HMHP guar), hydrophobically modified carboxymethylhydroxypropyl guar (HMCMHP guar) and hydrophobically modified cationic guar (HM cationic guar).

More preferred polysaccharides for use in preparing the compositions of this invention are carboxymethyl cellulose, carrageenan and pectin, or mixtures thereof. Most preferred is carboxymethyl cellulose.

The polyols used for agglomerating the water-soluble or water-swellable polymers include, but are not limited to, sugars, sugar alcohols, glycerol, polyethylene glycol, propylene glycol, and mixtures thereof.

Exemplary sugars are sucrose, glucose, lactose, fructose and xylose, or their mixtures. Exemplary sugar alcohols are sorbitol, inositol, mannitol, galactidol, arabitol, ribitol, xylitol and mixture thereof.

The preferred polyols for use in the invention are sorbitol and polyethylene glycol, or mixtures thereof. The molecular weight of the polyethylene glycols for use in the invention is not critical. Preferably the polyethylene glycols will have molecular weights of from about 200 to about 5,000,000, more preferably from about 600 to about 25,000, and most preferably from about 1,000 to about 10,000.

In the compositions of this invention the polyol used for agglomeration is at a level greater than about 10 wt. % based on the total weight of the composition. The maximum level of polyol is preferably about 90 wt. %, more preferably about 50 wt. %, and most preferably about 30 wt. %.

The agglomerated compositions may be prepared by spraying particulate polymer with polyol in liquid form. The polyol may be molten or in solution, preferably aqueous solution. In a preferred method the molten polyol or polyol solution is sprayed onto particles of water-soluble or water-swellable polymer in a fluidized bed while, if the polyol is in solution, simultaneously drying the particles. Commercially available fluidized bed spray units may be employed for the operation.

The agglomerated compositions of this invention hydrate or dissolve in water or water-containing solvents substantially faster without formation of polymer lumps than do the corresponding untreated water-soluble or water-swellable polymers. This hydration or dissolving rate is measured using a Haake Visco Tester 501, which measures the amount of torque (force) needed to maintain the rotation of the sensor in the solution at a set speed (400 rpm) as the polymer hydrates and thickening occurs. Hydration time is considered to be the time in minutes it takes to achieve 95% of final viscosity, where the final viscosity is taken as the average of the last 20 minutes viscosity during a two-hour trial.

In this work, hydration in water was determined at 55° C. For example, under the above conditions, untreated carboxymethyl cellulose lumped immediately and then required about 15 minutes to reach 95% viscosity; while carboxymethyl cellulose agglomerated by treatment with 20 wt. % sorbitol or 20 wt. % polyethylene glycol gave some immediate lumping which quickly dispersed and dissolved in less than one minute.

An added advantage of these compositions is that the agglomeration serves to reduce the amount of dusting that occurs when the untreated polymers are handled.

The toothpastes of this invention contain abrasives, humectants, and water-soluble polymer. Humectants are used to retain moisture in toothpaste, particularly at the nozzle end of the tube where the toothpaste can be in prolonged contact with air. The water-soluble polymers serve as thickeners and binders for the ingredients. A variety of other ingredients such as flavors, sweeteners, preservatives, detergents, tartar control agents, plaque control agents and fluoride may also be utilized at low levels.

The dental abrasives for use in the toothpastes of this invention are typically silicas and insoluble inorganic salts. Preferred inorganic salts are calcium carbonate, dibasic calcium phosphate, tribasic calcium phosphate, calcium sulfate, insoluble sodium metaphosphate, hydrated aluminum oxide, and magnesium carbonates and phosphates. Silicas and silica xerogels are particularly useful for translucent or transparent toothpastes.

Typical humectants for use in the toothpastes of this invention include glycerol, sorbitol, propylene glycol or mixtures thereof, which are mixed with a suitable humectant vehicle such as water.

In the toothpastes of this invention the agglomerated water-soluble or water-swellable polymer may contain polyol at a level of from about 0.5 to about 90 wt. % based on the total weight of the agglomerated water-soluble or water-swellable polymer. A preferred level is from about 2 to about 50 wt. %, and a more preferred level from about 10 to about 30 wt. %.

For preparation of the toothpastes of this invention, the water-soluble or water-swellable polymer which has been agglomerated by treatment with polyol is stirred with: a) humectant or a mixture of humectants; b) humectant vehicle, most typically water; c) salts, flavors, colorants, surfactants; and d) abrasive to obtain a complete toothpaste formulation. In a preferred method of preparation, the agglomerated water-soluble polymer is added directly to the mixture of humectants and humectant vehicle and stirred until the polymer particles are fully dissolved or swollen; then any salts are added, followed by abrasive. The abrasive is added after complete dissolution of the salts. The mixture is stirred until the particles of abrasive are wetted out; then the flavors are added, followed by surfactant.

This invention is illustrated by the following examples, which are for illustration only, and not intended to be limiting. All percentages, parts, etc., are by weight unless otherwise indicated.

Examples 1–14 demonstrate the preparation and testing of carrageenan and carboxymethyl cellulose agglomerated by treatment with polyethylene glycol or sorbitol. The carrageenan was GENU® carrageenan (available from Hercules Incorporated, Wilmington, Del.). Carboxymethyl cellulose was either CMC 7MF or CMC 7MXF (available from Hercules Incorporated, Wilmington, Del.).

The polymers were treated in a Glaft Fluid Bed Processor (Model GPCG-5) top spray unit with aqueous solutions (25, 33 and 50%) of polyethylene glycol, PEG 4600 and 1450 (Union Carbide, Carbowax® 4600 and 1450) to a final polyol level of approximately 20% by weight. They were also treated with sorbitol at the 10% and 20% level by application of a 70% aqueous solution of sorbitol.

In the operation, all aqueous polyol solutions were heated to 50° C. and metered in by calibrated pump and balance. The Glaft Fluid Bed Processor was preheated for all trials. A Schlick 945 nozzle was utilized with a filter shake cycle of 30/3 seconds, reduced to 2 minutes/3 seconds after increase in particle size. The atomization air pressure was set at 2 bar. All products were dried to about 6–8% moisture and then cooled to 30°–34° C. The batch size was 3 kg.

The agglomerated samples and the untreated controls were evaluated for their dispersibility and hydration/dissolution characteristics in deionized water at 55° C. using a Haake VT501 viscometer equipped with an FL 10 sensor. The instrument measures the amount of torque (force) needed to maintain the rotation of the sensor in the solution at the set speed (400 rpm) as the polymer hydrates and thickening occurs. The data are then mathematically converted by computer to viscosity (cps).

The hydration time reported in Table 1 is the time in minutes required to reach 95% viscosity when the viscosity of the last 20 minutes of a two hour run is taken as 100%. Each sample viscosity was run at 2% concentration based on total solution weight. No correction was made for the amount of polyol or moisture in the sample.

EXAMPLES 1–8 AND COMPARATIVE EXAMPLE A

These examples illustrate the agglomeration of carrageenan by treatment with sorbitol and with polyethylene glycol. The data are in Table 1. Comparative Example A is presented to show the hydration time for untreated carrageenan.

TABLE 1

Agglomerating Carrageenan by Treatment with Sorbitol or Poyethyene Gycol

| | | | Agglomeration Process | | |
|---|---|---|---|---|---|
| Example No. | Polyol | Polyol Level, wt. % | Spraying Rate, g/min. | Product Temp., °C. | Time to 95% Viscosity, min |
| 1 | Sorbitol (70% aq. sol.) | 20 | 34 | 50 | 3 |
| 2 | Sorbitol (70% aq. sol.) | 10 | 33 | 48 | 2 |
| 3 | PEG 4600 (50% aq. sol.) | 20 | 35–84 | 42–44 | 9 |
| 4[1] | PEG 4600 (33% aq. sol.) | 20 | 165 | 38 | <1 |
| 5 | PEG 4600 (50% aq. sol.) | 20 | 9–20 | 38–42 | 11 |
| 6 | Sorbitol (70% aq. sol.) | 10 | 12 | 56–62 | 30 |
| 7 | Sorbitol (70% aq. sol.) | 20 | 8 | 60 | 22 |
| 8 | Sorbitol (70% aq. sol.) | 20 | 9 | 40–42 | 23 |
| A[2] | — | — | — | — | 22 |

[1]In this example the carrageenan was preagglomerated by spraying a 3 kg batch with 1200 g of water at 170 g/min prior to spraying with PEG.
[2]Untreated carrageenan

EXAMPLES 9–14 AND COMPARATIVE EXAMPLES B AND C

These examples illustrate agglomeration of carboxymethyl cellulose by treatment with sorbitol and with polyethylene glycol. The data are in Table 2. Comparative Examples B and C are presented to show the hydration time for untreated carboxymethyl cellulose.

The data indicate that the hydration time of carboxymethyl cellulose is substantially reduced by agglomeration with sorbitol or polyethylene glycol at levels of 10% or above.

TABLE 2

Agglomeration of Carboxymethyl Cellulose with Sorbitol or Polyethylene Glycol

| | | Agglomeration Process | | | |
|---|---|---|---|---|---|
| Example No. | Polyol | Polyol Level, wt. % | Spraying Rate, g/min. | Product Temp., °C. | Time to 95% Viscosity, min |
| 9[1] | Sorbitol (70% aq. sol.) | 20 | 44 | 52 | <1 |
| 10[1] | Sorbitol (70% aq. sol.) | 20 | 8 | 41 | 6 |
| 11[1] | PEG 1450 (50% aq. sol.) | 20 | 150 | 38 | <1 |
| 12[1,3] | PEG 1450 (50% aq. sol.) | 20 | 90–100 | 38 | <1 |
| 13[2,4] | PEG 1450 (50% aq. sol.) | 20 | 165 | 38 | <1 |
| 14[1] | Sorbitol (70% aq. sol.) | 10 | 9 | 42 | 15 |
| B[1] | — | — | — | — | 15 |
| C[2] | — | — | — | — | 10 |

[1]Carboxymethyl cellulose is CMC 7MF (Hercules Incorporated).
[2]Carboxymethyl cellulose is CMC 7MXF (Hercules Incorporated).
[3]In this example the carboxymethyl cellulose was preagglomerated by spraying a 3 kg batch with 800 g of water at 120 g/min prior to spraying with PEG.
[4]In this example the carboxymethyl cellulose was preagglomerated by spraying a 3 kg batch with 1500 g of water at 70 g/min prior to spraying with PEG.

EXAMPLES 15 AND 16 AND COMPARATIVE EXAMPLES D AND E

These examples illustrate the formulation of toothpastes utilizing carboxymethyl cellulose agglomerated by treatment with sorbitol or polyethylene glycol. The comparative examples demonstrate formulation of control compositions where untreated carboxymethyl cellulose was used.

Examples 15 and 16 illustrate the preparation of toothpastes at room temperature using carboxymethyl cellulose CMC 7MF which was agglomerated by treatment with 9% sorbitol and 16% polyethylene glycol (PEG 1450) respectively. Comparative examples D and E demonstrate similar formulations where the CMC 7MF was untreated. The ingredients and ingredient levels for each formulation are listed in Table 3.

TABLE 3

Toothpaste Formulations, Wt. %

| Ingredient | Example 15 | Example 16 | Comparative Example D | Comparative Example E |
|---|---|---|---|---|
| CMC 7MF agglomerated with 9% sorbitol | 1.10 | | | |
| CMC 7MF agglomerated with 16% PEG 1450 | | 1.10 | | |
| CMC 7MF | | | 1.10 | 1.10 |
| Glycerol | | | 13.00 | |
| Sorbitol (70% aq. sol.) | 35.43 | 35.43 | 16.88 | 35.43 |
| Distilled Water | 8.79 | 8.79 | 14.36 | 8.79 |
| Dicalcium Phosphate, dihydrate | 45.0 | 45.0 | 45.0 | 45.0 |
| Tetrasodium Pyrophosphate | 0.42 | 0.42 | 0.42 | 0.42 |
| Sodium Saccharin | 0.20 | 0.20 | 0.20 | 0.20 |
| Sodium Monofluorophosphate | 0.76 | 0.76 | 0.76 | 0.76 |
| Sodium Benzoate | 0.50 | 0.50 | 0.50 | 0.50 |
| Distilled Water | 6.25 | 6.25 | 6.25 | 6.25 |
| Flavor | 0.55 | 0.55 | 0.55 | 0.55 |
| Sodium Lauryl sulfate | 1.00 | 1.00 | 1.00 | 1.00 |

For the glycerol-free formulations (Examples 15, 16 and Comparative Example E), the following procedure was used:

1. Tetra sodium pyrophosphate (0.42 parts), sodium saccharin (0.20 parts) sodium monofluorophosphate (0.76 parts) and sodium benzoate (0.50 parts) were added to 6.25 parts of water with stirring, and heated to about 60° C. to dissolve.

2. The carboxymethyl cellulose (1.10 parts) was added to the sorbitol solution (35.43 parts) in a beaker and stirred for 15 minutes or until adequately dispersed. The 8.79 parts of water was then added and the resulting mixture was stirred for 15 to 30 minutes making sure the polymer was completely hydrated (no gels). Then the warm salt solution from step 1 was added with stirring, which was continued for 15 minutes or until homogeneity (no lumps or gels). The mixture was then transferred to a Ross double planetary mixer.

3. The dicalcium phosphate dihydrate (DCP) (45.00 parts) was added to the mixer and mixing was continued for 10 minutes to completely wet the DCP. The mixer was then opened and the beaters and bowl sides were scraped down. The mixer was then closed; vacuum was applied; and mixing was continued at high speed for 20 minutes or until the mix was smooth.

4. The sodium lauryl sulfate (1.00 parts) was then added and mixing was continued for 5 minutes at low speed without vacuum. Then the flavor (0.55 parts) was added followed by mixing for 2 minutes at low speed. The mixer was then opened and the beaters and bowl sides were scraped down. The mixer was then closed; vacuum was applied; and mixing was continued at medium speed for 15 minutes. The mixer was then shut off; vacuum was broken; and toothpaste was packed out.

In Comparative Example D, where glycerol was utilized, the procedure was essentially the same as the above, with the exception that in step 2 the carboxymethyl cellulose was dispersed in the glycerol with stirring. Stirring was continued for 5 minutes or until the carboxymethyl cellulose was adequately dispersed. The sorbitol solution was then added and stirring was continued for another 10 minutes. The water (14.36 parts) was added and stirring was continued for 15 to 30 minutes making sure that the polymer was completely hydrated (no gels). The warm salt solution was added and stirring was continued for 15 minutes or until homogeneity (no lumps or gels). Then the mixture was transferred to the Ross mixer for the remaining steps.

In Examples 15 and 16 it was observed that the agglomerated carboxymethyl cellulose dispersed very easily in the aqueous sorbitol solution. Hydration of the polymer appeared to begin in about 3 to 4 minutes and proceeded slowly until addition of the water and salts solution. No lumping of the carboxymethyl cellulose was observed.

In comparative Example D, the untreated carboxymethyl cellulose dispersed easily in the anhydrous glycerol with no lumping. However, in comparative Example E, the untreated carboxymethyl cellulose dispersed in the sorbitol solution only with a very high rate of agitation. Hydration of the polymer appeared to begin in 1 to 2 minutes. Some lumping of the carboxymethyl cellulose was observed in the sorbitol/salts solution.

EXAMPLES 17 AND 18 AND COMPARATIVE EXAMPLES F AND G

These examples illustrate the formulation of toothpastes utilizing carboxymethyl cellulose agglomerated by treatment with sorbitol or with polyethylene glycol at 55° C. The comparative examples demonstrate formulation of control compositions where untreated carboxymethyl cellulose was used.

Examples 17 and 18 illustrate the preparation of toothpastes at room temperature using carboxymethyl cellulose CMC 7MF agglomerated by treatment with 9% sorbitol and with 16% polyethylene glycol (PEG 1450) respectively. Comparative examples F and G demonstrate similar formulations where the CMC 7MF was untreated. The ingredients and ingredient levels for each formulation are listed in Table 4.

TABLE 4

Toothpaste Formulations, Wt. %

| Ingredient | Example 17 | Example 18 | Comparative Example F | Comparative Example G |
|---|---|---|---|---|
| CMC 7MF agglomerated with 9% sorbitol | 1.00 | | | |
| CMC 7MF agglomerated with 16% PEG 1450 | | 1.00 | | |
| CMC 7MF | | | 1.00 | 1.00 |
| Glycerol | | | 13.00 | |
| Sorbitol (70% aq. sol.) | 35.43 | 35.43 | 16.86 | 35.43 |
| Distilled Water | 8.89 | 8.89 | 14.46 | 8.89 |
| Dicalcium Phosphate, dihydrate | 45.00 | 45.00 | 45.00 | 45.00 |
| Tetrasodium Pyrophosphate | 0.42 | 0.42 | 0.42 | 0.42 |
| Sodium Saccharin | 0.20 | 0.20 | 0.20 | 0.20 |
| Sodium Monofluorophosphate | 0.76 | 0.76 | 0.76 | 0.76 |
| Sodium Benzoate | 0.50 | 0.50 | 0.50 | 0.50 |
| Distilled Water | 6.25 | 6.25 | 6.25 | 6.25 |
| Flavor | 0.55 | 0.55 | 0.55 | 0.55 |
| Sodium Lauryl sulfate | 1.00 | 1.00 | 1.00 | 1.00 |

For the glycerol-free formulations (Examples 17 and 18 and Comparative Example G), the following procedure was used:

1. Tetra sodium pyrophosphate (0.42 parts), sodium saccharin (0.20 parts) sodium monofluorophosphate (0.76 parts) and sodium benzoate (0.50 parts) were added to 6.25 parts of water with stirring, and heated to about 60° C. to dissolve.

2. The sorbitol solution (35.43 parts) was heated to 55° C. and then the carboxymethyl cellulose (1.00 parts) was added with stirring which was continued for 15 minutes or until adequate dispersion was achieved. The water (8.89 parts), heated to 55° C., was then added, and stirring was continued for 15 to 30 minutes to ensure complete hydration of the polymer (no gels). Then the warm salt solution from step 1 was added with stirring, which was continued for 15 minutes or until homogeneity (no lumps or gels). The mixture was then transferred to a Ross double planetary mixer.

3. The dicalcium phosphate dihydrate (DCP) (45.00 parts) was added to the mixer and mixing was continued for 10 minutes to completely wet the DCP. The mixer was then opened and the beaters and bowl sides were scraped down. The mixer was then closed; vacuum was applied; and mixing was continued at high speed for 20 minutes or until the mix was smooth.

4. The sodium lauryl sulfate (1.00 parts) was then added and mixing was continued for 5 minutes at low speed without vacuum. Then the flavor (0.55 parts) was added followed by mixing for 2 minutes at low speed. The mixer was then opened and the beaters and bowl sides were scraped down. The mixer was then closed; vacuum was applied; and mixing was continued at medium speed for 15 minutes. The mixer was then shut off; vacuum was broken; and toothpaste was packed out.

The procedure for Comparative Example F differed from the above only in the second step. The carboxymethyl cellulose was dispersed in glycerol at 55° C. with stirring, which was continued for 5 minutes, or until adequate dispersion was achieved. Then the sorbitol solution was added and stirring continued for an additional 10 minutes. The water at 55° C. was then added with stirring for 15 to 30 minutes to ensure complete hydration (no gels), and then the warm salt solution from step 1 was added with stirring, which was continued for 15 minutes or until homogeneity (no lumps or gels). The mixture was then transferred to a Ross double planetary mixer.

In Examples 17 and 18 and in Comparative Example F, it was found that the carboxymethyl cellulose materials dispersed easily and evenly in hot sorbitol without lumping. Hydration of the polymer began after 1–2 minutes and proceeded rapidly after addition of water and salts solution. The resulting gel phases were very smooth and the resulting pastes were smooth creams. In contrast, in Comparative Example G, it was not possible to achieve a smooth dispersion of the untreated carboxymethyl cellulose. Even with a high rate of agitation severe lumping of the polymer could not be avoided.

EXAMPLE 19

This example illustrates preparation of toothpaste containing carrageenan agglomerated by treatment with 20% sorbitol.

| Ingredients: | |
|---|---|
| glycerol | 22 parts |
| carrageenan (agglomerated by treatment with 20% sorbitol) | 0.96 |
| sodium benzoate | 0.50 |
| sodium saccharin | 0.2 |
| tetrasodium pyrophosphate | 0.25 |
| sodium monofluorophosphate | 0.76 |
| deionized water | 21.28 |
| dicalcium phosphate | 51.75 |
| sodium lauryl sulfate | 1.50 |
| peppermint oil | 0.80 |

Procedure:

A dry blend of the sodium saccharin, sodium benzoate, agglomerated carrageenan, sodium monofluorophosphate, tetrasodium pyrophosphate was mixed with the glycerol and stirred for 5 minutes. Then the water was added, and the resulting mixture was heated at 66°–71° C. for 15 minutes. The weight was then adjusted back to original weight by addition of distilled water. The mixture was transferred to a Hobart mixer, the dicalcium phosphate was added, and the resulting mixture was stirred at mixer speed 1 for 2 minutes. The mixer was stopped; the bowl and blade were scraped down, and then mixing was resumed at speed 2 for 10 minutes.

The paste was transferred to a vacuum deaerating paddle; the sodium lauryl sulfate and flavor oil were added with mixing, and then the mixture was deaerated for 5 minutes at 0.98 bar. The resulting toothpaste was then packed into tubes for storage.

During this preparation, dispersion of the agglomerated carrageenan occurred rapidly without lump formation.

It is not intended that the examples presented here should be construed to limit the invention, but rather they are submitted to illustrate some of the specific embodiments of the invention. Various modifications and variations of the present invention can be made without departing from the scope of the appended claims.

What is claimed is:

1. A composition comprising particulate water-soluble or water-swellable polymer at least partially agglomerated by treatment with at least one polyol selected from the group consisting of sugar alcohols, glycerol, polyethylene glycol, propylene glycol, and mixtures thereof, wherein the polyol is at a level greater than about 10 wt. % based on the total weight of the composition, and wherein the composition is substantially dry.

2. The composition of claim 1 wherein the composition is dispersible in solvents substantially faster than untreated water-soluble or water-swellable polymer, without formation of polymer lumps.

3. The composition of claim 1 wherein the treatment comprises spraying the at least one polyol in liquid form onto particles of water-soluble or water-swellable polymer in a fluidized bed while simultaneously drying the particles.

4. The composition of claim 1 wherein the water-soluble or water-swellable polymer is at least one polysaccharide.

5. The composition of claim 4 wherein the polysaccharide is at least one member selected from the group consisting of cellulose ethers, guar, guar derivatives, locust bean gum, psyllium, gum arabic, gum ghatti, gum karaya, gum tragacanth, carrageenan, agar, algin, xanthan, scleroglucan, dextran, pectin, starch, chitin and chitosan.

6. The composition of claim 4 wherein the polysaccharide is at least one cellulose ether selected from the group consisting of hydroxyethyl cellulose (HEC), hydroxypropyl cellulose (HPC), water soluble ethylhydroxyethyl cellulose (EHEC), carboxymethyl cellulose (CMC), carboxymethylhydroxyethyl cellulose (CMHEC), hydroxypropylhydroxyethyl cellulose (HPHEC), methyl cellulose (MC), methylhydroxypropyl cellulose (MHPC), methylhydroxyethyl cellulose (MHEC), carboxymethylmethyl cellulose (CMMC), hydrophobically modified carboxymethyl cellulose (HMCMC), hydrophobically modified hydroxyethyl cellulose (HMHEC), hydrophobically modified hydroxypropyl cellulose (HMHPC), hydrophobically modified ethylhydroxyethyl cellulose (HMEHEC), hydrophobically modified carboxymethylhydroxyethyl cellulose (HMCMHEC), hydrophobically modified hydroxypropylhydroxyethyl cellulose (HMHPHEC), hydrophobically modified methyl cellulose (HMMC), hydrophobically modified methylhydroxypropyl cellulose (HMMHPC), hydrophobically modified methylhydroxyethyl cellulose (HMMHEC), hydrophobically modified carboxymethylmethyl cellulose (HMCMMC), cationic hydroxyethyl cellulose (cationic HEC) and cationic hydrophobically modified hydroxyethyl cellulose (cationic HMHEC).

7. The composition of claim 4 wherein the polysaccharide is at least one guar derivative selected from the group consisting of carboxymethyl guar (CM guar), hydroxyethyl guar (HE guar), hydroxypropyl guar (HP guar), carboxymethylhydroxypropyl guar (CMHP guar), cationic guar, hydrophobically modified guar (HM guar), hydrophobically modified carboxymethyl guar (HMCM guar), hydrophobically modified hydroxyethyl guar (HMHE guar), hydrophobically modified hydroxypropyl guar (HMHP guar), cationic hydrophobically modified hydroxypropyl guar (cationic HMHP guar), hydrophobically modified carboxymethylhydroxypropyl guar (HMCMHP guar) and hydrophobically modified cationic guar (HM cationic guar).

8. The composition of claim 4 wherein the polysaccharide is carboxymethyl cellulose.

9. The composition of claim 4 wherein the polysaccharide is carrageenan.

10. The composition of claim 4 wherein the polysaccharide is a mixture of carboxymethyl cellulose and carrageenan.

11. The composition of claim 1 wherein the polyol is selected from the group consisting of sorbitol, mannitol, galactidol, arabitol, ribitol, xylitol, glycerol, polyethylene glycol, propylene glycol, and mixtures thereof.

12. The composition of claim 1 wherein the polyol is selected from the group consisting of sorbitol, polyethylene glycol, and mixtures thereof.

13. The composition of claim 8 wherein the polyol is selected from the group consisting of sorbitol and polyethylene glycol, or mixtures thereof.

14. The composition of claim 9 wherein the polyol is selected from the group consisting of sorbitol and polyethylene glycol, or mixtures thereof.

15. The composition of claim 10 wherein the polyol is selected from the group consisting of sorbitol and polyethylene glycol, or mixtures thereof.

16. The composition of claim 1 wherein the maximum level of polyol is about 90 wt. % based on the total weight of the composition.

17. The composition of claim 16 wherein the maximum level of polyol is about 50 wt. % based on the total weight of the composition.

18. The composition of claim 17 wherein the maximum level of polyol is about 30 wt. % based on the total weight of the composition.

19. The composition of claim 1 wherein the water-soluble or water-swellable polymer is at least one member selected from the group consisting of carrageenan, carboxymethyl cellulose and mixtures thereof, and the polyol is at least one member selected from the group consisting of sorbitol, polyethylene glycol and mixtures thereof, wherein the maximum level of polyol is about 50 wt. % based on the total weight of the composition.

20. In a process for preparing a toothpaste composition comprising at least one dry, water-soluble or water-swellable polymer, the improvement comprising substituting for the dry, water-soluble or water-swellable polymer the composition of claim 1.

21. The process of claim 20 wherein the agglomerated water-soluble or water-swellable polymer hydrates in water or water-containing solvents substantially faster than untreated water-soluble or water-swellable polymer, without formation of polymer lumps.

22. The process of claim 20 wherein the water-soluble or water-swellable polymer is polysaccharide.

23. The process of claim 22 wherein the polysaccharide is at least one member selected from the group consisting of cellulose ethers, guar, guar derivatives, locust bean gum, psyllium, gum arabic, gum ghatti, gum karaya, gum tragacanth, carrageenan, agar, algin, xanthan, scleroglucan, dextran, pectin, starch, chitin and chitosan.

24. The process of claim 22 wherein the polysaccharide is at least one cellulose ether selected from the group consisting of hydroxyethyl cellulose (HEC), hydroxypropyl cellulose (HPC), water soluble ethylhydroxyethyl cellulose (EHEC), carboxymethyl cellulose (CMC), carboxymethylhydroxyethyl cellulose (CMHEC), hydroxypropylhydroxyethyl cellulose (HPHEC), methyl cellulose (MC), methylhydroxypropyl cellulose (MHPC), methylhydroxyethyl cellulose (MHEC), carboxymethylmethyl cellulose (CMMC), hydrophobically modified carboxymethyl cellulose (HMCMC), hydrophobically modified hydroxyethyl cellulose (HMHEC), hydrophobically modified hydroxypropyl cellulose (HMHPC), hydrophobically modified ethylhydroxyethyl cellulose (HMEHEC), hydrophobically modified carboxymethylhydroxyethyl cellulose (HMCMHEC), hydrophobically modified hydroxypropylhydroxyethyl cellulose (HMHPHEC), hydrophobically modified methyl cellulose (HMMC), hydrophobically modified methylhydroxypropyl cellulose (HMMHPC), hydrophobically modified methylhydroxyethyl cellulose (HMMHEC), hydrophobically modified carboxymethylmethyl cellulose (HMCMMC), cationic hydroxyethyl cellulose (cationic HEC) and cationic hydrophobically modified hydroxyethyl cellulose (cationic HMHEC).

25. The process of claim 22 wherein the polysaccharide is at least one guar derivative selected from the group consisting of carboxymethyl guar (CM guar), hydroxyethyl guar (HE guar), hydroxypropyl guar (HP guar), carboxymethylhydroxypropyl guar (CMHP guar), cationic guar, hydrophobically modified guar (HM guar), hydrophobically modified carboxymethyl guar (HMCM guar), hydrophobically modified hydroxyethyl guar (HMHE guar), hydrophobically modified hydroxypropyl guar (HMHP guar), cationic hydrophobically modified hydroxypropyl guar (cationic HMHP guar), hydrophobically modified carboxymethylhydroxypropyl guar (HMCMHP guar) and hydrophobically modified cationic guar (HM cationic guar).

26. The process of claim 22 wherein the polysaccharide is selected from the group consisting of carboxymethyl cellulose, carrageenan, pectin, and mixtures thereof.

27. The process of claim 22 wherein the polysaccharide is carboxymethyl cellulose.

28. The process of claim 22 wherein the polysaccharide is carrageenan.

29. The process of claim 22 wherein the polysaccharide is a mixture of carboxymethyl cellulose and carrageenan.

30. The process of claim 20 wherein the polyol is selected from the group consisting of sorbitol, mannitol, galactidol, arabitol, ribitol, xylitol, glycerol, polyethylene glycol, propylene glycol, and mixtures thereof.

31. The process of claim 20 wherein the polyol is selected from the group consisting of sorbitol, polyethylene glycol, and mixtures thereof.

32. The process of claim 27 wherein the polyol is selected from the group consisting of sorbitol, polyethylene glycol, and mixtures thereof.

33. The process of claim 29 wherein the polyol is selected from the group consisting of sorbitol, polyethylene glycol, and mixtures thereof.

34. The process of claim 28 wherein the polyol is selected from the group consisting of sorbitol, polyethylene glycol, and mixtures thereof.

35. The process of claim 20 wherein the toothpaste composition further comprises dental abrasive and humectant.

36. The process of claim 35 wherein the humectant is selected from the group consisting of glycerol, sorbitol, polyethylene glycol, propylene glycol, and mixtures thereof.

37. The process of claim 36 wherein the water-soluble or water-swellable polymer is carboxymethyl cellulose and the polyol is selected from the group consisting of sorbitol, polyethylene glycol, and mixtures thereof.

38. The process of claim 36 wherein the water-soluble or water-swellable polymer is carrageenan and the polyol is selected from the group consisting of sorbitol, polyethylene glycol, and mixtures thereof.

39. The process of claim 20 wherein the at least partially agglomerated particulate water-soluble or water-swellable polymer is prepared by spraying at least one polyol in liquid form onto particles of water-soluble or water-swellable polymer in a fluidized bed while simultaneously drying the particles.

40. The process of claim 39 wherein the polyol is in aqueous solution.

41. The process of claim 39 wherein the water-soluble or water-swellable polymer is at least one member selected from the group consisting of cellulose ethers, guar, guar derivatives and carrageenan.

42. The process of claim 39 wherein the water-soluble or water-swellable polymer is carboxymethyl cellulose.

43. The process of claim 39 wherein the water-soluble or water-swellable polymer is carrageenan.

44. The process of claim 39 wherein the water-soluble or water-swellable polymer is a mixture of carboxymethyl cellulose and carrageenan.

45. The process of claim 20 wherein the toothpaste composition further comprises ingredients selected from the group consisting of flavors, sweeteners, preservatives, surfactants, antibacterials, coloring agents, tartar control agents and fluoride.

46. The process of claim 20 wherein the polyol in the agglomerated water-soluble or water-swellable polymer is at a level of from about 0.5 to about 90 wt. % based on the total weight of the agglomerated water-soluble or water-swellable polymer.

47. The process of claim 46 wherein the polyol in the agglomerated water-soluble or water-swellable polymer is at a level of from about 2 to about 50 wt. % based on the total weight of the agglomerated water-soluble or water-swellable polymer.

48. The process of claim 47 wherein the polyol in the agglomerated water-soluble or water-swellable polymer is at a level of from about 10 to about 30 wt. % based on the total weight of the agglomerated water-soluble or water-swellable polymer.

49. Toothpaste made by the process of claim 20.

50. Toothpaste made by the process of claim 39.

51. Toothpaste made by the process of claim 31.

52. Toothpaste made by the process of claim 32.

53. Toothpaste made by the process of claim 33.

* * * * *